United States Patent [19]
Rose et al.

[11] Patent Number: 4,575,377
[45] Date of Patent: Mar. 11, 1986

[54] OXIDATION HAIR DYES COMPRISING RESORCINOL DERIVATIVES AS COUPLING COMPONENTS

[75] Inventors: David Rose, Hilden; Edgar Lieske, Düsseldorf, both of Fed. Rep. of Germany

[73] Assignee: Henkel Kommanditgesellschaft auf Aktien, Düsseldor-Holthausen, Fed. Rep. of Germany

[21] Appl. No.: 650,304

[22] Filed: Sep. 12, 1984

Related U.S. Application Data

[63] Continuation of Ser. No. 458,832, Jan. 18, 1983, abandoned.

[30] Foreign Application Priority Data

Sep. 10, 1982 [DE] Fed. Rep. of Germany ....... 3233541

[51] Int. Cl.$^4$ .............................................. A61K 7/13
[52] U.S. Cl. .......................................... 8/408; 8/409; 8/424
[58] Field of Search ........................... 8/408, 409, 424

[56] References Cited

U.S. PATENT DOCUMENTS

| Re. 30,199 | 1/1980 | Rose et al. | 8/409 |
| 3,861,868 | 1/1975 | Milbrada | 8/424 |
| 3,893,803 | 7/1975 | Kaiser | 8/408 |
| 3,957,424 | 5/1976 | Zeffren et al. | 8/424 |
| 4,003,699 | 1/1977 | Rose et al. | 8/409 |
| 4,129,413 | 12/1978 | Rose et al. | 8/409 |
| 4,213,758 | 7/1980 | Rose et al. | 8/409 |
| 4,289,495 | 9/1981 | Bugaut et al. | 8/408 |
| 4,479,803 | 10/1984 | Bachmann et al. | 8/408 |

FOREIGN PATENT DOCUMENTS

| 162625 | 11/1903 | Fed. Rep. of Germany . | |
| 276761 | 12/1912 | Fed. Rep. of Germany . | |
| 2717041 | 10/1978 | Fed. Rep. of Germany | 8/409 |
| 8100810 | 4/1981 | PCT Int'l Appl. | 8/424 |

Primary Examiner—Albert T. Meyers
Assistant Examiner—John M. Kilcoyne
Attorney, Agent, or Firm—Hammond & Littell, Weissenberger & Dippert

[57] ABSTRACT

This invention is directed to compositions of the developer-coupler type of the dyeing of hair consisting essentially of resorcinol derivatives or salts thereof as coupling components and, as developer components, the conventional components used in oxidation dyes.

15 Claims, No Drawings

OXIDATION HAIR DYES COMPRISING RESORCINOL DERIVATIVES AS COUPLING COMPONENTS

This application is a continuation of co-pending U.S. patent application Ser. No. 458,832, filed Jan. 18, 1983, now abandoned.

FIELD OF THE INVENTION

This invention is directed to oxidation hair dyes. More specifically, this invention is directed to the use of resorcinol derivatives as coupling components in oxidation hair dyes.

BACKGROUND OF THE INVENTION

Dyes known to oxidation dyes, which are produced by oxidative coupling of a developer component with a coupling component, are preferred due to their intense colors, the mild reaction conditions under which they are formed, and their very good fastness properties. Nitrogen bases such as primary aromatic amines with an additional hydroxyl or unsubstituted or substituted amino group in ortho or para position, diaminopyridine derivatives, 4-amino-pyrazolone derivatives, heterocyclic hydrazone derivatives, and tetraaminopyrimidines are generally used as developer substances. Phenols, m-phenylenediamine derivatives, naphthols, certain resorcinol derivatives, and pyrazolones are known to be useful as coupling components.

Good oxidation dyestuff components must meet the following requirements:

They must produce the desired color nuances in sufficient intensity during oxidative coupling with the respective developer or coupling component. Also, they must possess a capacity for being absorbed by human hair without excessive coloring of the scalp. In addition, they should be toxicologically and dermatologically safe.

The production of the strongest possible color shades closely corresponding to the natural hair color nuances is also important. Furthermore, the general stability of the dyestuffs produced as well as their fastness to light and to washing and their thermostability, have very special significance for the prevention of color shifts from the original color nuance or even a change in color to different shades. In addition, in the hair dyeing field there is always an interest in new oxidation dye components that can be combined with the known dye components to produce new color nuances of cosmetic value.

The use of resorcinol as a coupling component is known from German patent specification Nos. 162,625 and 276,761. Other resorcinol derivatives, for example, alkyl- and di-alkyl-m-dihydroxybenzenes, were suggested as coupling components for oxidation hair dyes in U.S. Pat. No. 4,003,699. However, the resistance characteristics of the hair colors obtainable with resorcinol and the known resorcinol derivatives are not satisfactory. For example, resorcinol and 2-methylresorcinol in combination with many conventional developer components, for example, with tetraaminopyrimidines, produce colors that have a tendency to turn red when they are exposed to light and heat.

Thus, the search for suitable oxidation hair dyes includes the task of finding the proper components that meet the above-mentioned prerequisites in an optimal fashion.

OBJECTS OF THE INVENTION

It is an object of the invention to provide agents for oxidative dyeing of hair that are based upon resorcinol derivatives as coupling components.

It is also an object of the invention to provide a process for dyeing hair wherein a novel hair dyestuff is employed.

These and other objects of the invention will become more apparent in the discussion below.

DETAILED DESCRIPTION OF THE INVENTION

Applicants have found novel hair dyestuffs that satisfy the above-mentioned requirements. The hair dyestuffs are based upon oxidation dyes comprising resorcinol derivatives of the formula

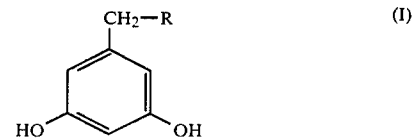

(I)

wherein R represents an amino, hydroxyl, or carboxyl group, or salts thereof with inorganic or organic acids or alkali metals, as coupling component, and as developer component, one or more of the conventional developer substances used in oxidation hair dyes. Such hair dyestuffs can meet the above-mentioned requirements to an especially high degree, and, in addition, surprisingly offer the advantage of increased resistance to undesirable red discoloration under the influence of light and/or heat.

Hair dyes according to the invention, that is, oxidation coupler/developer hair dyestuffs where the coupler substance comprises one or more compounds of Formula I, produce especially intense and bright hair colors with good lightfastness and resistance to heat, with nuances mainly in the brown range. The resorcinol derivatives of Formula I to be used according to the invention are compounds that are known from the literature.

The novel coupling substances of Formula I are suitable for a large number of different developer systems, and particularly valuable color nuances are obtained when aromatic or heterocyclic diamines are used as developer substances.

Examples of useful developer components include primary aromatic amines with an additional functional group in the p-position, such as p-phenylenediamine, p-toluylenediamine, p-aminophenol, N-methyl-p-phenylenediamine, N,N-dimethyl-p-phenylenediamine, N,N-diethyl-2-methyl-p-phenylenediamine, N-ethyl-N-(2-hydroxyethyl)-p-phenylenediamine, chloro-p-phenylenediamine, N,N-bis-(2-hydroxyethyl)-p-phenylenediamine, methoxy-p-phenylenediamine, 2,5-diaminoanisole, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, N-(2-hydroxypropyl)-p-phenylenediamine, and N-(2-methoxyethyl)-p-phenylenediamine, and other compounds of this type which also contain one or more additional functional groups such as hydroxyl groups, amino groups, or —NHR or —NR$_2$ groups in which R represents an alkyl with from 1 to 4 carbon atoms or a hydroxyalkyl with from 2 to 4 carbon atoms. Diaminopyridine derivatives, heterocyclic hydrazone derivatives such as 1-methyl-pyrrolidon-(2)-hydrozone, 4-aminopyrazolone derivatives such as 4-amino-1-phenyl-3-carbamoyl-pyrazolone-5, N-butyl-N-sulfobutyl-p-phenylenediamine, and tetraaminopyrimidine derivatives comprise additional examples of useful developer components.

More specifically, tetraaminopyrimidine derivatives suitable as developers comprise compounds of the formula

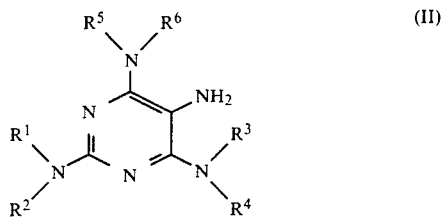

wherein $R^1$ to $R^6$ may each be a hydrogen atom; an alkyl with from 1 to 4 carbon atoms; or the radical —$(CH_2)_n X$ in which n is an integer of from 1 to 4 and X is selected from the group consisting of a hydroxyl group, a halogen atom, and —$NR^7 R^8$ in which $R^7$ and $R^8$ are each a hydrogen atom or an alkyl having from 1 to 4 carbon atoms or together with the nitrogen atom $R^7$ and $R^8$ form a 5- or 6-membered heterocyclic ring of carbon atoms and the nitrogen atom, optionally containing an additional nitrogen or oxygen atom in the ring in place of a carbon atom, or each of $R^1$ and $R^2$, $R^3$ and $R^4$, and $R^5$ and $R^6$ may with the nitrogen atom to which they are attached form a 5- or 6-membered heterocyclic ring of carbon atoms and the nitrogen atom, optionally containing an additional nitrogen or oxygen atom in the ring in place of a carbon atom, or an inorganic or organic salt thereof, is used as developer component.

The compound 2,4,5,6,-tetraaminopyrimidine and its derivatives are known as developer components in hair dyes from U.S. Pat. No. Re. 30,199, incorporated herein by reference.

Specific examples of tetraaminopyrimidines of Formula II include the following:
2,4,5,6-tetraaminopyrimidine,
4,5-diamino-2,6-bis-methylaminopyrimidine,
2,5-diamino-4,6-bis-methylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5-diamino-6-methylamino-2-piperidinopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-β-hydroxyethylaminopyrimidine,
2,5,6-triamino-2-β-amino-ethylaminopyrimidine,
2,5,6-triamino-4-β-methylamino-ethylaminopyrimidine,
2,5-diamino-4,6-bis-γ-diethylamino-propylaminopyrimidine,
4,5-diamino-2-methylamino-6-(2-hydroxyethyl)-aminopyrimidine,
5-amino-2,4,5-triethylaminopyrimidine, and
2,4-bis-β-hydroxyethylamino-6-anilino-5-aminopyrimidine.

The tetraaminopyrimidines of Formula II can be used as such or in the form of their salts with inorganic or organic acids, for example, as chlorides, sulfates, phosphates, acetates, propionates, lactates, or citrates.

The resorcinol derivatives of Formula I to be used as coupling components according to the invention can be used either as such or in the form of their salts with inorganic or organic acids or alkali metals, for example, as hydrochlorides, sulfates, phosphates, acetates, propionates, lactates, or citrates. In addition, the resorcinol derivatives of Formula I can be used together with additional, known coupling substances for hair dye products, such as, for example, naphthols; resorcinol derivatives such as 2-methylresorcinol or 4-chlororesorcinol; pyrazolones; phenols; or m-phenylenediamine derivatives. Also, conventional, directly attaching dyes such as, for example, nitrophenylenediamine derivatives, can be added to modify the color nuances.

In the hair dyestuffs according to the invention, the coupling and developer components generally are used in approximately equimolar amounts. Although the equimolar use proves suitable, it is not disadvantageous to add the coupling component in a certain excess or deficiency. For example, the coupling and developer components can be present in a molar range of from about 2:1 to 1:2, a 10% or less excess or deficiency being preferred.

In addition, it is not necessary that the developer component and the coupling substance are homogeneous or pure products. On the contrary, the developer component may consist of mixtures of the developer compounds to be used according to the invention, and the coupling substance may be in the form of mixtures of resorcinol derivatives or salts thereof according to the invention.

The oxidative coupling, that is, the development of the dye, can in principle be carried out with atmospheric oxygen, as is done with other oxidation hair dyestuffs also. However, chemical oxidation agents are advantageously employed. Particularly suitable as such oxidation agents are hydrogen peroxide or its adducts with urea, melamine, or sodium borate as well as mixtures of such hydrogen peroxide adducts with potassium peroxydisulfate.

For the preparation of the hair dyes according to the invention, the oxidation dye intermediate products are incorporated into suitable cosmetic preparations such as, for example, creams, emulsions, gels, foam aerosols, foaming solutions containing tensides, such as shampoos, or other products suitable for application to the hair. Conventional components of such cosmetic preparations include, for example, wetting and emulsifying agents such as anionic, nonionic, or ampholytic tensides, for example, sulfates of fatty alcohols, alkane sulfonates, α-olefin sulfonates, polyglycol ether sulfates of fatty alcohols, adducts of ethylene oxide onto fatty alcohols, fatty acids, or alkyl phenols, sorbitan fatty acid esters, partial glycerides of fatty acids, and alkanolamides of fatty acids; thickeners such as methyl or hydroxyethyl cellulose, starch, fatty alcohols, liquid paraffin, or fatty acids; perfume oils; and hair-conditioning and grooming additives such as water-soluble cationic polymers, protein derivatives, pantothenic acid, or cholesterol.

The above-mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, upon the total weight of the hair dye preparation. The concentration of the oxidation dye intermediate products, that is, the coupler/developer combination, in the hair dye preparations is from about 0.2 to 5 percent by weight, preferably from about 1 to 3 percent by weight, based upon the weight of the total weight of the hair dye preparation.

A hair dye according to the invention can be applied in a weakly acid, neutral, or particularly alkaline medium at a pH of from 8 to 10, regardless of whether it is in the form of a solution, an emulsion, a cream, or a gel. The application temperatures range from about 15° to 40° C.

After the dye is allowed to react for a sufficient time, usually approximately 30 minutes, the preparation is removed by rinsing from the dyed hair. The hair is then washed with a mild shampoo and dried. Shampooing would be unnecessary if the hair dye preparation itself, for example, a coloring shampoo, has a high tenside content. The hair, which can be any color or length, can be either "live" hair or hair that has been cut, such as that in a wig.

The colors that can be achieved with the hair dyes according to the invention show a strong brilliance as well as superior resistance, that is, fastness, to heat.

The following examples are intended to illustrate the invention and are not to be construed as limiting the invention thereto.

EXAMPLES

The following resorcinol derivatives of Formula I were used as coupling components in oxidation hair dyes:

K-1: 3,5-hydroxybenzyl alcohol (synthesis according to Th. Boehm et al., Archiv der Pharmazie, Vol. 270 (1932), page 175)

K-2: 3,5-dihydroxybenzylamine (synthesis according to M. Ikeda et al., Tetrahedron, Vol. 33 (1977), page 491)

K-3: 3,5-dihydroxyphenlacetic acid (synthesis according to Theilacker et al., Annalen der Chemie, Vol. 570 (1950), page 27)

The following substances were used as developer components:

E-1: 2,4,5,6-tetraaminopyrimidine
E-2: p-phenylenediamine
E-3: p-toluylenediamine
E-4: 2,5-diaminoanisole
E-5: 2-chloro-o-phenylenediamine
E-6: N-ethyl-N-(2-hydroxyethyl)-p-phenylenediamine
E-7: N-butyl-N-sulfobutyl-p-phenylenediamine
E-8: N,N-bis-(2-hydroxyethyl)-p-phenylenediamine
E-9: N-methyl-p-phenylenediamine
E-10: N-(2-methoxyethyl)-p-phenylenediamine
E-11: N-(2-hydroxypropyl)-p-phenylenediamine
E-12: p-aminophenol Procedure The hair dyes according to the invention were used in the form of a cream emulsion. For this, 0.0075 mol of each of the developer substances and coupling substances listed in the table below were worked into an emulsion containing 10 parts by weight of fatty alcohols having 12 to 18 carbon atoms,
25 parts by weight of $C_{12-14}$-fatty alcohol+2EO-sulfate, Na-salt (28% active)
1 part by weight of $Na_2SO_3$ (as inhibitor), and
60 parts by weight of water.

Then, the pH of the emulsion was adjusted to 9.5 with ammonia, and the emulsion was made up to 100 parts by weight with water. Oxidative coupling was carried out with a 3% hydrogen peroxide solution acting as oxidation agent, 50 parts by weight of the hydrogen peroxide solution being added to 100 parts by weight of the emulsion.

After addition of the oxidation agents, the particular dyeing cream, with additional oxidation agent, was applied to 5-cm lengths of standardized human hair which was 90% gray and which had not been specially pretreated, and the cream was left on the hair for 30 minutes at about 27° C. After completion of the dyeing process, the hair was rinsed, washed with a conventional commercial shampoo, and dried. The colorations obtained by this process are compiled in the table below:

TABLE

| Example | Coupling Agent | Developer | Shade of Dyed Hair after Oxidation with 3% $H_2O_2$ Solution |
|---------|----------------|-----------|--------------------------------------------------------------|
| 1 | K-1 | E-1 | red brown |
| 2 | K-1 | E-2 | dark violet |
| 3 | K-1 | E-3 | dark brown |
| 4 | K-1 | E-4 | dark magenta |
| 5 | K-1 | E-5 | medium brown |
| 6 | K-1 | E-6 | gray ruby |
| 7 | K-1 | E-7 | gray brown |
| 8 | K-1 | E-8 | gray brown |
| 9 | K-1 | E-9 | nutria |
| 10 | K-1 | E-10 | gray brown |
| 11 | K-1 | E-11 | gray brown |
| 12 | K-1 | E-12 | brown |
| 13 | K-2 | E-1 | violet brown |
| 14 | K-2 | E-3 | dark brown |
| 15 | K-3 | E-1 | orange brown |
| 16 | K-3 | E-3 | brown |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An oxidation hair dye composition for the dyeing of human hair, comprising (a) at least one compound selected from the group consisting of 3,5-dihydroxybenzyl alcohol, 3,5-dihydroxybenzylamine and 3,5-dihydroxyphenyl acetic acid, or a salt thereof with an inorganic or organic acid or an alkali metal, as coupling component, and (b) a developer component, the coupling and developer components being present in a molar ratio of from about 2:1 to 1:2.

2. The composition of claim 1, wherein developer component (b) comprises one or more aromatic or heterocyclic diamines.

3. The composition of claim 1, wherein developer component (b) comprises one or more tetraaminopyrimidine derivatives of the formula

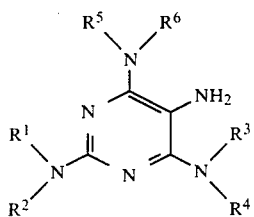

wherein $R^1$ to $R^6$ may each be a hydrogen atom; an alkyl with from 1 to 4 carbon atoms; or the radical $-(CH_2)_nX$ in which n is an integer of from 1 to 4 and X is selected from the group consisting of a hydroxyl group, a halogen atom, and $-NR^7R^8$ in which $R^7$ and $R^8$ are each a hydrogen atom or an alkyl having from 1 to 4 carbon atoms or together with the nitrogen atom $R^7$ and $R^8$ form a 5- or 6-membered heterocyclic ring of carbon atoms and the nitrogen atom, optionally containing an additional nitrogen or oxygen atom in the ring in place of a carbon atom, or each of $R^1$ and $R^2$, $R^3$ and $R^4$, and $R^5$ and $R^6$ may with the nitrogen atom to which they are attached form a 5- or 6-membered heterocyclic ring of carbon atoms and the nitrogen atom, optionally containing an additional nitrogen or oxygen atom in the ring in place of a carbon atom, or salts thereof with inorganic or organic acids.

4. The composition of claim 1, wherein the composition comprises from about 0.2 to 5 percent by weight of developer-coupler combination.

5. The composition of claim 4, wherein the composition comprises from about 1 to 3 percent by weight of developer-coupler combination.

6. A process for the dyeing of human hair comprising applying to said hair, at temperatures ranging substantially from about 15° to 40° C. for a time sufficient to effect dyeing through oxidation, an effective amount of the developer-coupler composition of claim 1 in an aqueous medium.

7. The process for the dyeing of hair of claim 6, wherein the oxidation is effected by the action of a chemical oxidation agent.

8. An oxidation hair dye composition for the dyeing of human hair, comprising:
(a) as coupling component, at least one compound selected from the group consisting of 3,5-dihydroxybenzyl alcohol, 3,5-dihydroxybenzylamine and 3,5-dihydroxyphenyl acetic acid, and
(b) as developer component, at least one compound selected from the group consisting of p-phenylenediamine, p-toluylenediamine, p-aminophenol, N-methyl-p-phenylenediamine, N,N-dimethyl-p-phenylenediamine, N,N-diethyl-2-methyl-p-phenylenediamine, N-ethyl-N-(2-hydroxyethyl)-p-phenylenediamine, chloro-p-phenylenediamine, N,N-bis-(2-hydroxyethyl)-p-phenylenediamine, methoxy-p-phenylenediamine, 2,5-diaminoanisole, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, N-(2-hydroxypropyl)-p-phenylenediamine, and N-(2-methoxyethyl)-p-phenylenediamine, either unsubstituted or substituted with one or more additional amino groups or $-NHR$ or $NR^2$ groups in which R represents an alkyl with from 1 to 4 carbon atoms or a hydroxyalkyl with from 2 to 4 carbon atoms; diaminopyridine derivatives; N-butyl-N-sulfobutyl-p-phenylenediamine; 2,4,5,6-tetraaminopyrimidine, 4,5-diamino-2,6-bis-methylaminopyrimidine; 2,5-diamino-4-diethylamino-6-methylaminopyrimidine; 2,4,5-triamino-6-dimethylaminopyrimidine; 2,4,5-triamino-6-piperidinopyrimidine; 2,4,5-triamino-6-anilinopyrimidine; 2,4,5-triamino-6-morpholino-pyrimidine; and 2,4,5-triamino-6-β-hydroxyethylaminopyrimidine.
the molar ratio of coupling component (a) to developer component (b) being from about 2:1 to 1:2.

9. The composition of claim 8 which additionally contains one or more couplers selected from the group consisting of 2-methylresorcinol and 4-chlororesorcinol.

10. An aqueous preparation of the developer-coupler type for the dyeing of human hair consisting essentially of from about 0.2 to 5 percent by weight of the developer-coupler composition of claim 8, from 0.5 to about 30 percent by weight of wetting and emulsifying agents, from 0.1 to about 25 percent by weight of a thickener, and the remainder water.

11. The preparation of claim 10 which contains from about 1 to 3 percent by weight of the developer-coupler composition.

12. A process for the dyeing of human hair comprising applying to said hair, at temperatures ranging substantially from about 15° to 40° C. for a time sufficient to effect dyeing through oxidation, an effective amount of the developer-coupler composition of claim 8 in an aqueous medium.

13. The process for the dyeing of hair of claim 12, wherein the oxidation is effected by the action of a chemical oxidation agent.

14. In an oxidation hair dye composition for the dyeing of human hair comprising one or more resorcinol derivatives as coupler component and one or more aromatic or heterocyclic diamines as developer component, the improvement wherein the coupler component comprises 3,5-dihydroxybenzyl alcohol, 3,5-dihydroxybenzylamine, 3,5-dihydroxyphenyl acetic acid or a mixture of two or more thereof, the coupler and developer components being present in a molar ratio of from about 2:1 to 1:2.

15. A process for the dyeing of human hair comprising applying to said hair, at temperatures ranging substantially from about 15° to 40° C. for a time sufficient to effect dyeing through oxidation, an effective amount of the developer-coupler composition of claim 14 in an aqueous medium.

* * * * *

UNITED STATES PATENT AND TRADEMARK OFFICE
CERTIFICATE OF CORRECTION

PATENT NO. : 4,575,377
DATED : March 11, 1986
INVENTOR(S) : DAVID ROSE et al.

It is certified that error appears in the above-identified patent and that said Letters Patent is hereby corrected as shown below:

Column 4, line 12, the moiety "2,5,6-" should read -- 4,5,6- --.

Signed and Sealed this

Eighth Day of July 1986

[SEAL]

*Attest:*

DONALD J. QUIGG

*Attesting Officer*     *Commissioner of Patents and Trademarks*